United States Patent
During

(10) Patent No.: US 10,653,652 B2
(45) Date of Patent: May 19, 2020

(54) USE OF (1S,3S)-3-AMINO-4-(DIFLUOROMETHYLIDENE)CYCLOPENTANE-1-CARBOXYLIC ACID AND (S)-3-AMINO-4-(DIFLUOROMETHYLENYL)CYCLOPENT-1-ENE-1-CARBOXYLIC ACID IN THE TREATMENT OF TINNITUS, ACUTE SENSORINEURAL HEARING LOSS, MENIERE'S DISEASE, TOURETTE'S SYNDROME, ATTENTION DEFICIT HYPERACTIVITY DISORDER AND ADDICTION

(71) Applicant: Ovid Therapeutics Inc., New York, NY (US)

(72) Inventor: Matthew During, Weston, CT (US)

(73) Assignee: Ovid Therapeutics Inc., New York, NY (US)

(*) Notice: Subject to any disclaimer, the term of this patent is extended or adjusted under 35 U.S.C. 154(b) by 0 days.

(21) Appl. No.: 16/270,856

(22) Filed: Feb. 8, 2019

(65) Prior Publication Data
US 2019/0240174 A1    Aug. 8, 2019

Related U.S. Application Data

(60) Provisional application No. 62/628,020, filed on Feb. 8, 2018, provisional application No. 62/628,541, filed on Feb. 9, 2018.

(51) Int. Cl.
*A61K 31/196* (2006.01)
*A61P 27/16* (2006.01)

(52) U.S. Cl.
CPC ............ *A61K 31/196* (2013.01); *A61P 27/16* (2018.01)

(58) Field of Classification Search
None
See application file for complete search history.

(56) References Cited

U.S. PATENT DOCUMENTS

| | | | |
|---|---|---|---|
| 6,656,172 B1 * | 12/2003 | Hildebrand | A61K 31/00 128/898 |
| 6,794,413 B1 * | 9/2004 | Silverman | A61K 31/557 514/573 |
| 8,969,413 B2 | 3/2015 | Silverman et al. | |
| 9,670,141 B2 | 6/2017 | Silverman et al. | |
| 9,993,449 B2 | 6/2018 | Silverman et al. | |
| 2007/0179168 A1 | 8/2007 | Cowley et al. | |
| 2013/0041028 A1 | 2/2013 | Silverman et al. | |
| 2013/0230586 A1 | 9/2013 | Coelho et al. | |
| 2014/0303243 A1 | 10/2014 | Hakonarson et al. | |
| 2014/0336256 A1 * | 11/2014 | Miller | A61K 31/195 514/561 |
| 2016/0271098 A1 | 9/2016 | Knipper et al. | |
| 2017/0101364 A1 | 4/2017 | Silverman et al. | |
| 2017/0239202 A1 | 8/2017 | Silverman et al. | |
| 2018/0221319 A1 | 8/2018 | During | |
| 2018/0271816 A1 | 9/2018 | Silverman et al. | |

FOREIGN PATENT DOCUMENTS

WO    2017062942 A2    4/2017

OTHER PUBLICATIONS

Le et al., "Design and Mechanism of Tetrahydrothiophene-Based gamma-Aminobutyric Acid Aminotransferase Inactivators," ACS 2015.*
Fornaro et al., "Tinnitus psychopharmacology: A comprehensive review of its pathomechanisms and management," Neuropsychiatric Disease and Treatment, May 29, 2010.*
Lippert, et al., "4-Amino-hex-5-enoic Acid, a Selective Catalytic Inhibitor of 4-Aminobutyric-Acid Aminotransferase in Mammalian Brain", Eur. J. Biochem,vol. 74, No. 3; Apr. 15, 1977; pp. 441-445.
Dewey et al., "A Novel Strategy for the Treatment of Cocaine Addiction", Synapse, vol. 30, No. 2, Oct. 1998; pp. 119-129.
Dewey et al., "A Pharmacologic Strategy for the Treatment of Nicotine Addiction", Synapse, vol. 31, No. 1, Jan. 1999; pp. 76-86.
Gerasimov et al., "Gamma-Vinyl GABA Inhibits Methamphetamine, Heroin, or Ethanol-Induced Increases in Nucleus Accumbens Dopamine", Synapse, vol. 34, No. 1, Oct. 1999; pp. 11-19.
Pan et al., "Design, Synthesis, and Biological Activity of a Difluoro-Substituted, Conformationally Rigid Vigabatrin Analogue as a Potent γ-Aminobutyric Acid Aminotransferase Inhibitor", Journal of Medicinal Chemistry, vol. 46, No. 25, Dec. 4, 2003;pp. 5292-5293.
International Search Report and Written Opinion of the International Searching Authority, corresponding to International Application No. PCT/US2016/056245, dated Jan. 26, 2017; 16 total pages.
Lu, et al., "Fluorinated Conformationally-Restricted γ-Aminobutyric Acid Aminotransferase Inhibitors", Journal of Medicinal Chemistry, E-Pub, vol. 49, No. 25, Oct. 11, 2006; pp. 7404-7412 and Figures 1-2.
Kanth et al., "QSAR Analysis of a Few GABA Aminotransferase Inhibitors as Potent Antiepileptics", Indian Journal of Chemistry, vol. 44B, Mar. 2005; pp. 595-599.
Chebib et al., "The Effects of Cyclopentane and Cyclopentene Analogues of GABA at Recombinant GABAC Receptors", European Journal of Pharmacology, vol. 430, No. 2-3; Nov. 2001; pp. 185-192.
Notification concerning Transmittal of International Preliminary Report on Patentability (Chapter I of the Patent Cooperation Treaty), dated Apr. 10, 2018, including International Preliminary Report on Patentability and Written Opinion of the International Searching Authority, corresponding to International Application No. PCT/US2016/056245; 13 total pages.

(Continued)

*Primary Examiner* — Jared Barsky
(74) *Attorney, Agent, or Firm* — Carter, DeLuca & Farrell LLP

(57) ABSTRACT

Methods of treating tinnitus, acute sensorineural hearing loss, Meniere's disease, Tourette's syndrome, ADHD or addiction with (1S,3S)-3-amino-4-(difluoromethylidene)cyclopentane-1-carboxylic acid or a pharmaceutically acceptable salt thereof are provided. Methods of treating tinnitus, acute sensorineural hearing loss, Meniere's disease, Tourette's syndrome, ADHD or addiction with (S)-3-amino-4-(difluoromethylenyl)cyclopent-1-ene-1-carboxylic acid are provided. Also provided are therapeutic compositions that may be used to improve one or more symptoms of tinnitus, acute sensorineural hearing loss, Meniere's disease, Tourette's syndrome, ADHD or addiction.

7 Claims, No Drawings

(56) References Cited

OTHER PUBLICATIONS

Tolman et al., "Treatment options for refractory and difficult to treat seizures: focus on vigabatrin", (Dovepress) Therapeutics and Clinical Risk Management, 2011, vol. 7; pp. 367-375.

Jozwiak et al., "Antiepileptic treatment before the onset of seizures reduces epilepsy severity and risk of mental retardation in infants with tuberous sclerosis complex", (Elsevier) Official Journal of the European Paediatric Neurology Society, European Journal of Paediatric Neurology 15 (2011); pp. 424-431.

Richard B. Silverman, "The 2011 E. B. Hershberg Award for Important Discoveries in Medicinally Active Substances: (1S, 3S)-3-Amino-4-difluoromethylenyl-1-cyclopentanoic Acid (CPP-115), a GABA Aminotransferase in activator and New Treatment for Drug Addiction and Infantile Spasms," Journal of Medicinal Chemistry, (2012), vol. 55; pp. 567-575.

Blume et al., ILAE Commission Report, Glossary of Descriptive Terminology for Ictal Semiology: Report of the ILAE Task Force on Classification and Terminology, Blackwell Science, Inc., International League Against Epilepsy, Epilepsia, (2001), vol. 42, No. 9; pp. 1212-1218.

International Search Report and Written Opinion, dated Apr. 16, 2018, corresponding to International Application No. PCT/US2018/017382; 8 pages.

International Search Report and Written Opinion, dated Jun. 17, 2019, corresponding to International Application No. PCT/US2019/017201; 11 pages.

* cited by examiner

USE OF (1S,3S)-3-AMINO-4-(DIFLUOROMETHYLIDENE) CYCLOPENTANE-1-CARBOXYLIC ACID AND (S)-3-AMINO-4-(DIFLUOROMETHYLENYL) CYCLOPENT-1-ENE-1-CARBOXYLIC ACID IN THE TREATMENT OF TINNITUS, ACUTE SENSORINEURAL HEARING LOSS, MENIERE'S DISEASE, TOURETTE'S SYNDROME, ATTENTION DEFICIT HYPERACTIVITY DISORDER AND ADDICTION

CROSS-REFERENCE TO RELATED APPLICATION

This application claims benefit of and priority to U.S. Provisional Application No. 62/628,020, filed Feb. 8, 2018 and U.S. Provisional Application No. 62/628,541, filed Feb. 9, 2018, which are incorporated herein by reference in their entireties.

TECHNICAL FIELD

Methods of treating tinnitus, acute sensorineural hearing loss, Meniere's disease, Tourette's syndrome, attention deficit hyperactivity disorder or addiction.

BACKGROUND

Tinnitus is characterized by an auditory sensation in the absence of external sound. In many cases tinnitus is subjectively perceptual, i.e., only the subject can perceive symptoms. Symptoms of tinnitus include ringing, roaring, static, buzzing, hissing and whistling in one or both ears. The noise may be intermittent or continuous. According to the National Institute on Deafness and other Communication Disorders (NIDCD) approximately 10 percent of the US adult population, or about 25 million Americans, have experienced some degree of tinnitus. According to the American Tinnitus Association, 20 million of these sufferers struggle with burdensome chronic tinnitus, while 2 million have extreme and debilitating cases. Severe tinnitus can lead to depression and other mental health challenges that severely affect the patient and the patient's family members. Therapies such as masking, sound therapy, electrical stimulation, and drugs have shown some benefit. Unfortunately, these treatments may be insufficient and many patients continue to suffer with tinnitus. Therefore, treatment of tinnitus remains a significant need.

Acute sensorineural hearing loss (ASNHL) is also known as sudden sensorineural hearing loss (SSNHL), sudden deafness and acute sensory hearing loss. Idiopathic acute sensorineural hearing loss is a form of acute sensorineural hearing loss in which no clear cause is known. The terms "acute sensorineural hearing loss" or "ASNHL" will be used herein for convenience and encompasses SSNHL, sudden deafness, acute sensory hearing loss and idiopathic acute sensorineural hearing loss. In certain instances, acute sensorineural hearing loss may be defined as the onset of one-sided sensorineural hearing loss in less than 72 hours. It strikes an estimated 5-20/100,000 persons per year. In some instances, ASNHL may occur following various inner ear injuries. In certain instances, ASNHL may be provoked by exposure to excessive noise (acoustic trauma, acute or otherwise), viral or bacterial infections in the inner ear, disturbances of the inner ear blood supply, middle and inner ear surgery, exposure to ototoxic drugs, head trauma, a tumor on the nerve that connects the ear to the brain and a variety of other incidents. In certain instances, ASNHL may be associated with surgery induced acoustic trauma. The most common complaint in ASNHL is a feeling of aural fullness (sometimes described as pressure in the ear), followed by complaints of hearing loss and tinnitus. Aural fullness is a non-specific symptom. The most common treatment for ASNHL, especially in cases where the cause is unknown, is corticosteroids. Corticosteroids may be associated with lowered immune response, which could be detrimental in cases where ASNHL is caused by bacterial or viral infection.

Meniere's disease is a disorder of the inner ear that causes episodes of vertigo and fluctuating hearing loss with a progressive, ultimately permanent loss of hearing, ringing in the ear (tinnitus), and sometimes a feeling of fullness or pressure in the affected ear. A common symptom of Meniere's disease is hypersensitivity to sounds. In many cases, Meniere's disease affects only one ear, at least initially; however, over time both ears may become involved. The cause of Meniere's disease is unclear but may involve both genetic and environmental factors. Meniere's disease has been associated with an abnormal amount of fluid (endolymph) in the inner ear. Although there is no cure for Meniere's disease, medications to reduce nausea such as dimenhydrinate, meclizine or prochlorperazine may be administered. Anti-inflammatory medications such as NSAIDS or corticosteroids may also be administered.

Tourette syndrome (TS) is a neurological disorder characterized by repetitive, stereotyped, involuntary movements and vocalizations called tics. The first symptoms of TS are almost always noticed in childhood, usually appearing between the ages of 3 and 12. Some of the more common tics include eye blinking and other vision irregularities, throat clearing, grunting, facial grimacing, shoulder shrugging, and head or shoulder jerking. Perhaps the most dramatic and disabling tics are those that result in self-harm such as punching oneself, or vocal tics including coprolalia (uttering swear words) or echolalia (repeating the words or phrases of others). Medications may be administered to control some symptoms of TS. For example, typical and atypical neuroleptics including risperidone, ziprasidone, haloperidol, pimozide and fluphenazine may be utilized but can have long-term and short-term adverse effects. Antihypertensive agents such as clonidine and guanfacine are also used to treat tics.

Attention-deficit/hyperactivity disorder (ADHD) is a brain disorder marked by an ongoing pattern of inattention and/or hyperactivity-impulsivity that interferes with functioning or development. According to the DSM-5 (2013) criteria for ADHD include six or more symptoms of inattention and six or more symptoms of hyperactivity and impulsivity for children up to age 16, or 5 or more such symptoms for adolescents 17 or older and adults. Inattention symptoms include: 1. often failure to give close attention to details or make careless mistakes in schoolwork, at work, or with other activities, 2. often has trouble holding attention on tasks or play activities, 3. often does not seem to listen when spoken to directly, 4. often does not follow through on instructions and fails to finish schoolwork, chores, or duties in the workplace (e.g., loses focus, side-tracked), 5. often has trouble organizing tasks and activities, 6. often easily distracted, and 7. often forgetful in daily activities. Hyperactivity and impulsivity symptoms include: 1. often fidgets with or taps hands or feet, or squirms in seat, 2. often leaves seat in situations when remaining seated is expected, 3. often runs about or climbs in situations where it is not appropriate (adolescents or adults may be limited to feeling restless), 4. often unable to play or take part in leisure activities quietly, 5. Is often "on the go" acting as if "driven by a motor", 6. often talks excessively, 7. often interrupts or intrudes on others (e.g., butts into conversations or games), 8. often blurts out an answer before a question has been completed. Medications may be administered to control some symptoms of ADHD. Stimulants such as methylphenidate, methamphetamine, dextroamphetamine, may be prescribed but can have adverse effects such as diminished appetite and headaches. non-stimulant medications, such as atomoxetine, bupropion, guanfacine, and clonidine that may be used as alternatives, or added to stimulant therapy.

Addiction is a brain disorder characterized by compulsive engagement in rewarding stimuli despite adverse consequences. Addiction is a disorder of the brain's reward system which arises through transcriptional and epigenetic mechanisms and occurs over time from chronically high levels of exposure to an addictive stimulus (e.g., eating food, the use of drugs, engagement in sexual intercourse, participation in high-thrill cultural activities such as gambling, etc.). Classic symptoms of addiction include impaired control over substances or behavior, preoccupation with substance or behavior, and continued use despite consequences. Habits and patterns associated with addiction are typically characterized by immediate gratification (short-term reward), coupled with delayed deleterious effects (long-term costs). Examples of drug and behavioral addictions include: alcoholism, amphetamine addiction, cocaine addiction, nicotine addiction, opiate addiction, benzodiazepine addiction, food addiction, gambling addiction, and sexual addiction. Pharmacological treatments for alcohol addiction include drugs like naltrexone, disulfiram, acamprosate, and topiramate. Opiate addiction may be treated with narcotic antagonists or replacement drugs such as buprenorphine and methadone. Currently, there are no medications approved for treatment of behavioral addictions in general, but some medications used for treatment of drug addiction may also be beneficial with specific behavioral addictions. Gabapentin and pregabalin may be used in connection with treatment for addiction.

SUMMARY

Methods of treating tinnitus are provided and, in embodiments, include administering to a subject in need thereof an effective amount of (1S,3S)-3-amino-4-(difluoromethylidene) cyclopentane-1-carboxylic acid or a pharmaceutically acceptable salt thereof. In embodiments, methods of treating tinnitus include administering (1S,3S)-3-amino-4-(difluoromethylidene) cyclopentane-1-carboxylic acid or a pharmaceutically acceptable salt thereof to a subject in need thereof to provide improvement in next day tinnitus in the subject. In embodiments, methods of treating tinnitus include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating tinnitus include administering (S)-3-amino-4-(difluoromethylenyl)cyclopent-1-ene-1-carboxylic acid or a pharmaceutically acceptable salt thereof to a subject in need thereof to provide improvement in one or more symptoms of the tinnitus. In embodiments, methods of treating tinnitus include administering (S)-3-amino-4-(difluoromethylenyl)cyclopent-1-ene-1-carboxylic acid or a pharmaceutically acceptable salt thereof to a subject in need thereof to provide improvement in next day tinnitus in the subject.

In embodiments, methods of treating tinnitus include administering: (1S,3S)-3-amino-4-(difluoromethylidene)cyclopentane-1-carboxylic acid or a pharmaceutically acceptable salt thereof, and (S)-3-amino-4-(difluoromethylenyl) cyclopent-1-ene-1-carboxylic acid or a pharmaceutically acceptable salt thereof, to a subject in need thereof.

In embodiments, methods of treating tinnitus are described herein which include administering to a patient in need thereof (1S,3S)-3-amino-4-(difluoromethylidene) cyclopentane-1-carboxylic acid or a pharmaceutically acceptable salt thereof in combination with a benzodiazepine wherein the method provides improvement in tinnitus. In embodiments, methods of treating tinnitus are described herein which include administering to a patient in need thereof of (S)-3-amino-4-(difluoromethylenyl) cyclopent-1-ene-1-carboxylic acid or a pharmaceutically acceptable salt thereof in combination with a benzodiazepine wherein the method provides improvement in tinnitus. In embodiments the benzodiazepine is clobazam.

In embodiments, methods of treating acute sensorineural hearing loss described herein include administering to a patient in need thereof (1S,3S)-3-amino-4-(difluoromethylidene) cyclopentane-1-carboxylic acid or a pharmaceutically acceptable salt thereof wherein the method provides improvement in acute sensorineural hearing loss. In embodiments, methods of treating acute sensorineural hearing loss described herein include administering to a patient in need thereof (S)-3-amino-4-(difluoromethylenyl) cyclopent-1-ene-1-carboxylic acid or a pharmaceutically acceptable salt thereof wherein the method provides improvement in acute sensorineural hearing loss. In embodiments, methods of treating acute sensorineural hearing loss described herein include administering to a patient in need thereof (1S,3S)-3-amino-4-(difluoromethylidene) cyclopentane-1-carboxylic acid or a pharmaceutically acceptable salt thereof in combination with a benzodiazepine wherein the method provides improvement in acute sensorineural hearing loss. In embodiments, methods of treating acute sensorineural hearing loss described herein include administering to a patient in need thereof (S)-3-amino-4-(difluoromethylenyl) cyclopent-1-ene-1-carboxylic acid or a pharmaceutically acceptable salt thereof in combination with a benzodiazepine wherein the method provides improvement in acute sensorineural hearing loss. In embodiments the benzodiazepine is clobazam.

In embodiments, methods of treating Meniere's disease described herein include administering to a patient in need thereof (1S,3S)-3-amino-4-(difluoromethylidene) cyclopentane-1-carboxylic acid or a pharmaceutically acceptable salt thereof wherein the method provides improvement in Meniere's disease. In embodiments, methods of treating Meniere's disease described herein include administering to a patient in need thereof (S)-3-amino-4-(difluoromethylenyl) cyclopent-1-ene-1-carboxylic acid or a pharmaceutically acceptable salt thereof wherein the method provides improvement in Meniere's disease. In embodiments, methods of treating Meniere's disease described herein include administering to a patient in need thereof (1S,3S)-3-amino-4-(difluoromethylidene) cyclopentane-1-carboxylic acid or a pharmaceutically acceptable salt thereof in combination with a benzodiazepine wherein the method provides improvement in Meniere's disease. In embodiments, methods of treating Meniere's disease described herein include administering to a patient in need thereof (S)-3-amino-4-(difluoromethylenyl) cyclopent-1-ene-1-carboxylic acid or a pharmaceutically acceptable salt thereof in combination with a benzodiazepine wherein the method provides improvement in Meniere's disease. In embodiments the benzodiazepine is clobazam.

In embodiments, methods of treating Tourette's syndrome described herein include administering to a patient in need thereof (1S,3S)-3-amino-4-(difluoromethylidene) cyclopentane-1-carboxylic acid or a pharmaceutically acceptable salt thereof wherein the method provides improvement in Tourette's syndrome. In embodiments, methods of treating Tourette's syndrome described herein include administering to a patient in need thereof (S)-3-amino-4-(difluoromethylenyl) cyclopent-1-ene-1-carboxylic acid or a pharmaceutically acceptable salt thereof wherein the method provides improvement in Tourette's syndrome. In embodiments, methods of treating Tourette's syndrome described herein include administering to a patient in need thereof (1S,3S)-3-amino-4-(difluoromethylidene) cyclopentane-1-carboxylic acid or a pharmaceutically acceptable salt thereof in combination with risperidone, ziprasidone, haloperidol, pimozide, fluphenazine, clonidine or guanfacine, wherein the method provides improvement in Tourette's syndrome. In embodiments, methods of treating Tourette's syndrome described herein include administering to a patient in need thereof (S)-3-amino-4-(difluoromethylenyl) cyclopent-1-ene-1-carboxylic acid or a pharmaceutically acceptable salt thereof in combination with risperidone, ziprasidone, haloperidol, pimozide, fluphenazine, clonidine or guanfacine, wherein the method provides improvement in Tourette's syndrome.

In embodiments, methods of treating ADHD described herein include administering to a patient in need thereof (1S,3S)-3-amino-4-(difluoromethylidene) cyclopentane-1-carboxylic acid or a pharmaceutically acceptable salt thereof wherein the method provides improvement in ADHD. In embodiments, methods of treating ADHD described herein include administering to a patient in need thereof (S)-3-amino-4-(difluoromethylenyl) cyclopent-1-ene-1-carboxylic acid or a pharmaceutically acceptable salt thereof wherein the method provides improvement in ADHD. In embodiments, methods of treating ADHD described herein include administering to a patient in need thereof (1S,3S)-3-amino-4-(difluoromethylidene) cyclopentane-1-carboxylic acid or a pharmaceutically acceptable salt thereof in combination with methylphenidate, methamphetamine, dextroamphetamine, atomoxetine, bupropion, guanfacine, or clonidine, wherein the method provides improvement in ADHD. In embodiments, methods of treating ADHD described herein include administering to a patient in need thereof (S)-3-amino-4-(difluoromethylenyl) cyclopent-1-ene-1-carboxylic acid or a pharmaceutically acceptable salt thereof in combination with methylphenidate, methamphetamine, dextroamphetamine, atomoxetine, bupropion, guanfacine, or clonidine, wherein the method provides improvement in ADHD.

In embodiments, methods of treating addiction described herein include administering to a patient in need thereof (1S,3S)-3-amino-4-(difluoromethylidene) cyclopentane-1-carboxylic acid or a pharmaceutically acceptable salt thereof wherein the method provides improvement in addiction. In embodiments, methods of treating addiction described herein include administering to a patient in need thereof (S)-3-amino-4-(difluoromethylenyl) cyclopent-1-ene-1-carboxylic acid or a pharmaceutically acceptable salt thereof wherein the method provides improvement in addiction. In embodiments, methods of treating addiction described herein include administering to a patient in need thereof (1S,3S)-3-amino-4-(difluoromethylidene) cyclopentane-1-carboxylic acid or a pharmaceutically acceptable salt thereof in combination with naltrexone, disulfiram, acamprosate, topiramate, buprenorphine, methadone, gabapentin or pregabalin, wherein the method provides improvement in addiction. In embodiments, methods of treating addiction described herein include administering to a patient in need thereof (S)-3-amino-4-(difluoromethylenyl) cyclopent-1-ene-1-carboxylic acid or a pharmaceutically acceptable salt thereof in combination with naltrexone, disulfiram, acamprosate, topiramate, buprenorphine, methadone, gabapentin or pregabalin, wherein the method provides improvement in addiction. In embodiments, the addiction is one or more of alcoholism, amphetamine addiction, cocaine addiction, nicotine addiction, opiate addiction, benzodiazepine addiction, food addiction, gambling addiction, and sexual addiction.

DETAILED DESCRIPTION

Described herein are methods and compositions for treating tinnitus which include administering to a subject in need thereof an effective amount of (1S,3S)-3-amino-4-(difluoromethylidene)cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods and compositions for treating acute sensorineural hearing loss which include administering to a subject in need thereof an effective amount of (1S,3S)-3-amino-4-(difluoromethylidene)cyclopentane-1-carboxylic acid or a pharmaceutically acceptable salt thereof, or (S)-3-amino-4-(difluoromethylenyl) cyclopent-1-ene-1-carboxylic acid or a pharmaceutically acceptable salt thereof, or combinations of the foregoing. Also described herein are methods and compositions for treating Meniere's disease which include administering to a subject in need thereof an effective amount of (1S,3 S)-3-amino-4-(difluoromethylidene)cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods and compositions for treating Tourette's syndrome which include administering to a subject in need thereof an effective amount of (1S,3 S)-3-amino-4-(difluoromethylidene)cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods and compositions for treating Attention deficit hyperactivity disorder (ADHD) which include administering to a subject in need thereof an effective amount of (1S,3 S)-3-amino-4-(difluoromethylidene)cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods and compositions for treating addiction which include administering to a subject in need thereof an effective amount of (1S,3S)-3-amino-4-(difluoromethylidene)cyclopentane-1-carboxylic acid or a pharmaceutically acceptable salt thereof, or (S)-3- amino-4-(difluoromethylenyl)cyclopent-1-ene-1-carboxylic acid or a pharmaceutically acceptable salt thereof, or combinations of the foregoing.

Described herein are methods of treating tinnitus with (1S,3S)-3-amino-4-(difluoromethylidene)cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods of treating acute sensorineural hearing loss with (1S,3S)-3-amino-4-(difluoromethylidene)cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereon, or combinations of the foregoing. Also described herein are methods of treating Meniere's disease with (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods of treating Tourette's syndrome with (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods of treating ADHD with (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing. Also described herein are methods of treating addiction with (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing.

Methods of treating tinnitus are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating tinnitus include administering (1S,3S)-3-amino-4-(difluoromethylidene)cyclopentane-1-carboxylic acid or a pharmaceutically acceptable salt thereof to a subject in need thereof to provide improvement in one or more symptoms of the tinnitus in the subject. In embodiments, methods of treating tinnitus include administering (1S,3S)-3-amino-4-(difluoromethylidene)cyclopentane-1-carboxylic acid or a pharmaceutically acceptable salt thereof to a subject in need thereof to provide improvement in next day tinnitus symptoms of the subject. In embodiments, methods of treating tinnitus include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating tinnitus include administering (S)-3-amino-4-(difluoromethylenyl)cyclopent-1-ene-1-carboxylic acid or a pharmaceutically acceptable salt thereof to a subject in need thereof to provide improvement in one or more symptoms of the tinnitus. In embodiments, methods of treating tinnitus include administering (S)-3-amino-4-(difluoromethylenyl)cyclopent-1-ene-1-carboxylic acid or a pharmaceutically acceptable salt thereof to a subject in need thereof to provide improvement in next day tinnitus symptoms of the subject. In embodiments, methods of treating tinnitus include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

Methods of treating acute sensorineural hearing loss are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating acute sensorineural hearing loss include administering (1S,3S)-3-amino-4-(difluoromethylidene)cyclopentane-1-carboxylic acid or a pharmaceutically acceptable salt thereof to a subject in need thereof to provide improvement in one or more symptoms of the acute sensorineural hearing loss. In embodiments, methods of treating acute sensorineural hearing loss include administering (1S,3S)-3-amino-4-(difluoromethylidene)cyclopentane-1-carboxylic acid or a pharmaceutically acceptable salt thereof to a subject in need thereof to provide improvement in next day acute sensorineural hearing loss of the subject. In embodiments, methods of treating acute sensorineural hearing loss include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating acute sensorineural hearing loss include administering (S)-3-amino-4-(difluoromethylenyl)cyclopent-1-ene-1-carboxylic acid or a pharmaceutically acceptable salt thereof to a subject in need thereof to provide improvement in one or more symptoms of the acute sensorineural hearing loss. In embodiments, methods of treating acute sensorineural hearing loss include administering (S)-3-amino-4-(difluoromethylenyl)cyclopent-1-ene-1-carboxylic acid or a pharmaceutically acceptable salt thereof to a subject in need thereof to provide improvement in next day acute sensorineural hearing loss of the subject. In embodiments, methods of treating acute sensorineural hearing loss include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

Methods of treating Meniere's disease are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating Meniere's disease include administering (1S,3S)-3-amino-4-(difluoromethylidene)cyclopentane-1-carboxylic acid or a pharmaceutically acceptable salt thereof to a subject in need thereof to provide improvement in one or more symptoms of the Meniere's disease. In embodiments, methods of treating Meniere's disease include administering (1S,3S)-3-amino-4-(difluoromethylidene)cyclopentane-1-carboxylic acid or a pharmaceutically acceptable salt thereof to a subject in need thereof to provide improvement in next day Meniere's disease symptoms of the subject. In embodiments, methods of treating Meniere's disease include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating Meniere's disease include administering (S)-3-amino-4-(difluoromethylenyl)cyclopent-1-ene-1-carboxylic acid or a pharmaceutically acceptable salt thereof to a subject in need thereof to provide improvement in one or more symptoms of the Meniere's disease. In embodiments, methods of treating Meniere's disease include administering (S)-3-amino-4-(difluoromethylenyl)cyclopent-1-ene-1-carboxylic acid or a pharmaceutically acceptable salt thereof to a subject in need thereof to provide improvement in next day Meniere's disease symptoms of the subject. In embodiments, methods of treating Meniere's disease include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

Methods of treating Tourette's syndrome are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating Tourette's syndrome include administering (1S,3S)-3-amino-4-(difluoromethylidene)cyclopentane-1-carboxylic acid or a pharmaceutically acceptable salt thereof to a subject in need thereof to provide improvement in one or more symptoms of the Tourette's syndrome in the subject. In embodiments, methods of treating Tourette's syndrome include administering (1S,3S)-3-amino-4-(difluoromethylidene)cyclopentane-1-carboxylic acid or a pharmaceutically acceptable salt thereof to a subject in need thereof to provide improvement in next day Tourette's syndrome symptoms of the subject. In embodiments, methods of treating Tourette's syndrome include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating Tourette's syndrome include administering (S)-3-amino-4-(difluoromethylenyl)cyclopent-1-ene-1-carboxylic acid or a pharmaceutically acceptable salt thereof to a subject in need thereof to provide improvement in one or more symptoms of the Tourette's syndrome. In embodiments, methods of treating Tourette's syndrome include administering (S)-3-amino-4-(difluoromethylenyl)cyclopent-1-ene-1-carboxylic acid or a pharmaceutically acceptable salt thereof to a subject in need thereof to provide improvement in next day Tourette's syndrome symptoms of the subject. In embodiments, methods of treating Tourette's syndrome include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

Methods of treating ADHD are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating ADHD include administering (1S,3S)-3-amino-4-(difluoromethylidene)cyclopentane-1-carboxylic acid or a pharmaceutically acceptable salt thereof to a subject in need thereof to provide improvement in one or more symptoms of the ADHD in the subject. In embodiments, methods of treating ADHD include administering (1S,3S)-3-amino-4-(difluoromethylidene)cyclopentane-1-carboxylic acid or a pharmaceutically acceptable salt thereof to a subject in need thereof to provide improvement in next day ADHD symptoms of the subject. In embodiments, methods of treating ADHD include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating ADHD include administering (S)-3-amino-4-(difluoromethylenyl)cyclopent-1-ene-1-carboxylic acid or a pharmaceutically acceptable salt thereof to a subject in need thereof to provide improvement in one or more symptoms of the ADHD. In embodiments, methods of treating ADHD include administering (S)-3-amino-4-(difluoromethylenyl)cyclopent-1-ene-1-carboxylic acid or a pharmaceutically acceptable salt thereof to a subject in need thereof to provide improvement in next day ADHD symptoms of the subject. In embodiments, methods of treating ADHD include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

Methods of treating addiction are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating addiction include administering (1S,3S)-3-amino-4-(difluoromethylidene)cyclopentane-1-carboxylic acid or a pharmaceutically acceptable salt thereof to a subject in need thereof to provide improvement in one or more symptoms of the addiction in the subject. In embodiments, methods of treating addiction include administering (1S,3S)-3-amino-4-(difluoromethylidene)cyclopentane-1-carboxylic acid or a pharmaceutically acceptable salt thereof to a subject in need thereof to provide improvement in next day addiction symptoms of the subject. In embodiments, methods of treating addiction include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating addiction include administering (S)-3-amino-4-(difluoromethylenyl)cyclopent-1-ene-1-carboxylic acid or a pharmaceutically acceptable salt thereof to a subject in need thereof to provide improvement in one or more symptoms of the addiction. In embodiments, methods of treating tinnitus include administering (S)-3-amino-4-(difluoromethylenyl)cyclopent-1-ene-1-carboxylic acid or a pharmaceutically acceptable salt thereof to a subject in need thereof to provide improvement in next day addiction symptoms of the subject. In embodiments, methods of treating addiction include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

The structure of (1S,3S)-3-amino-4-(difluoromethylidene)cyclopentane-1-carboxylic acid may be represented as follows:

The structure of (S)-3-amino-4-(difluoromethylenyl)cyclopent-1-ene-1-carboxylic acid may be represented as follows:

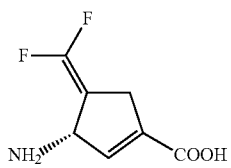

In embodiments, provided herein are methods of treating tinnitus including administering to a patient in need thereof a pharmaceutical composition including (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or a combination of the foregoing, wherein the composition provides improvement in at least one symptom of the tinnitus. Symptoms of tinnitus may include, but are not limited to, ringing, roaring, static, buzzing, hissing, whooshing, cricket noises, jackhammer noises and/or whistling in one or both ears. The symptoms may be intermittent or continuous.

In embodiments, provided herein are methods of treating acute sensorineural hearing loss including administering to a patient in need thereof a pharmaceutical composition including (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing, wherein the composition provides improvement in at least one symptom of the acute sensorineural hearing loss. Symptoms of acute sensorineural hearing loss may include, but are not limited to, hearing loss, aural fullness, and tinnitus.

In embodiments, provided herein are methods of treating Meniere's disease including administering to a patient in need thereof a pharmaceutical composition including (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing, wherein the composition provides improvement in at least one symptom of the Meniere's disease. Symptoms of Meniere's disease may include, but are not limited to, vertigo, hearing loss, tinnitus, hypersensitivity to sounds, and aural fullness in the affected ear.

In embodiments, provided herein are methods of treating Tourette's syndrome including administering to a patient in need thereof a pharmaceutical composition including (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or a combination of the foregoing, wherein the composition provides improvement in at least one symptom of the Tourette's syndrome. Symptoms of Tourette's syndrome are tics which may include eye blinking and other vision irregularities, throat clearing, grunting, facial grimacing, shoulder shrugging, and head or shoulder jerking, self-harm, and vocal tics including coprolalia or echolalia.

In embodiments, provided herein are methods of treating ADHD including administering to a patient in need thereof a pharmaceutical composition including (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or a combination of the foregoing, wherein the composition provides improvement in at least one symptom of the ADHD. Symptoms of ADHD are inattention and/or hyperactivity-impulsivity that interferes with functioning or development. Inattention symptoms may include: 1. often failure to give close attention to details or make careless mistakes in schoolwork, at work, or with other activities, 2. often has trouble holding attention on tasks or play activities, 3. often does not seem to listen when spoken to directly, 4. often does not follow through on instructions and fails to finish schoolwork, chores, or duties in the workplace (e.g., loses focus, sidetracked), 5. often has trouble organizing tasks and activities, 6. often easily distracted, and 7. often forgetful in daily activities. Hyperactivity and impulsivity symptoms may include: 1. often fidgets with or taps hands or feet, or squirms in seat, 2, often leaves seat in situations when remaining seated is expected, 3. often runs about or climbs in situations where it is not appropriate (adolescents or adults may be limited to feeling restless), 4. often unable to play or take part in leisure activities quietly, 5. Is often "on the go" acting as if "driven by a motor", 6. often talks excessively, 7. often interrupts or intrudes on others (e.g., butts into conversations or games), 8. often blurts out an answer before a question has been completed.

In embodiments, provided herein are methods of treating addiction including administering to a patient in need thereof a pharmaceutical composition including (1S,3S)-3-amino-4-(difluoromethylidene) cyclopentane-1-carboxylic acid or a pharmaceutically acceptable salt thereof, or (S)-3-amino-4-(difluoromethylenyl)cyclopent-1-ene-1-carboxylic acid or a pharmaceutically acceptable salt thereof, or combinations of the foregoing, wherein the composition provides improvement in at least one symptom of the addiction. Symptoms of addiction may include, but are not limited to, compulsive engagement in rewarding stimuli despite adverse consequences, impaired control over substances or behavior, preoccupation with substance or behavior, continued use despite consequences, immediate gratification (short-term reward), coupled with delayed deleterious effects (long-term costs). Examples of drug and behavioral addictions include alcoholism, amphetamine addiction, cocaine addiction, nicotine addiction, opiate addiction, benzodiazepine addiction, food addiction, gambling addiction, and sexual addiction.

As used herein, the terms "effective amount" or "therapeutically effective amount" refer to an amount of a compound, material, composition, medicament, or other material that is effective to achieve a particular pharmacological and/or physiologic effect in connection with tinnitus symptoms. Likewise, the terms "effective amount" or "therapeutically effective amount" refer to an amount of a compound, material, composition, medicament, or other material that is effective to achieve a particular pharmacological and/or physiologic effect in connection with acute sensorineural hearing loss. Likewise, the terms "effective amount" or "therapeutically effective amount" refer to an amount of a compound, material, composition, medicament, or other material that is effective to achieve a particular pharmacological and/or physiologic effect in connection with Meniere's disease. Likewise, the terms "effective amount" or "therapeutically effective amount" refer to an amount of a compound, material, composition, medicament, or other material that is effective to achieve a particular pharmacological and/or physiologic effect in connection with Tourette's syndrome. Likewise, the terms "effective amount" or "therapeutically effective amount" refer to an amount of a compound, material, composition, medicament, or other material that is effective to achieve a particular pharmacological and/or physiologic effect in connection with ADHD. Likewise, the terms "effective amount" or "therapeutically effective amount" refer to an amount of a compound, material, composition, medicament, or other material that is effective to achieve a particular pharmacological and/or physiologic effect in connection with addiction.

Accordingly, an effective amount of (1S,3S)-3-amino-4-(difluoromethylidene)cyclopentane-1-carboxylic acid or a pharmaceutically acceptable salt thereof is used to treat a subject having tinnitus. An effective amount of (1S,3S)-3-amino-4-(difluoromethylidene)cyclopentane-1-carboxylic acid or a pharmaceutically acceptable salt thereof is used to treat a subject having acute sensorineural hearing loss. An effective amount of (1S,3S)-3-amino-4-(difluoromethylidene)cyclopentane-1-carboxylic acid or a pharmaceutically acceptable salt thereof is used to treat a subject having Meniere's disease. An effective amount of (S)-3-amino-4-(difluoromethylenyl)cyclopent-1-ene-1-carboxylic acid or a pharmaceutically acceptable salt thereof is used to treat a subject having tinnitus. An effective amount of (S)-3-amino-4-(difluoromethylenyl)cyclopent-1-ene-1-carboxylic acid or a pharmaceutically acceptable salt thereof is used to treat a subject having acute sensorineural hearing loss. An effective amount of (S)-3-amino-4-(difluoromethylenyl)cyclopent-1-ene-1-carboxylic acid or a pharmaceutically acceptable salt thereof is used to treat a subject having Meniere's disease. Accordingly, an effective amount of (1S,3S)-3-amino-4-(difluoromethylidene)cyclopentane-1-carboxylic acid or a pharmaceutically acceptable salt thereof is used to treat a subject having Tourette's syndrome. An effective amount of (1S,3S)-3-amino-4-(difluoromethylidene)cyclopentane-1-carboxylic acid or a pharmaceutically acceptable salt thereof is used to treat a subject having ADHD. An effective amount of (1S,3S)-3-amino-4-(difluoromethylidene)cyclopentane-1-carboxylic acid or a pharmaceutically acceptable salt thereof is used to treat a subject having addiction. An effective amount of (S)-3-amino-4-(difluoromethylenyl)cyclopent-1-ene-1-carboxylic acid or a pharmaceutically acceptable salt thereof is used to treat a subject having Tourette's syndrome. An effective amount of (S)-3-amino-4-(difluoromethylenyl)cyclopent-1-ene-1-carboxylic acid or a pharmaceutically acceptable salt thereof is used to treat a subject having ADHD. An effective amount of (S)-3-amino-4-(difluoromethylenyl)cyclopent-1-ene-1-carboxylic acid or a pharmaceutically acceptable salt thereof is used to treat a subject having addiction.

The subject may be an animal, e.g., mammal, e.g., human, etc. As used herein, the terms "treat", "treatment" or "treating" encompass any manner in which the symptoms or pathology of a condition, disorder or disease associated with tinnitus, acute sensorineural hearing loss, Meniere's disease, Tourette's syndrome, ADHD or addiction are ameliorated or otherwise beneficially altered. In embodiments, "treat", "treatment" or "treating" can refer to inhibiting a disease or condition, e.g., arresting or reducing its development or at least one clinical or subclinical symptom thereof. In embodiments, "treat", "treatment" or "treating" can refer to relieving the disease or condition, e.g., causing regression of the disease or condition or at least one of its clinical or subclinical symptoms. The benefit to a subject being treated may be statistically significant, mathematically significant, or at least perceptible to the subject and/or the physician.

The effective amount can vary according to a variety of factors such as subject-dependent variables (e.g., age, immune system, health, etc.), the disease or disorder being treated, as well as the route of administration and the pharmacokinetics of the agent being administered.

Many pharmaceutical products are administered as a fixed dose, at regular intervals, to achieve therapeutic efficacy. Duration of action is typically reflected by a drug's plasma half-life. Since efficacy is often dependent on sufficient exposure within the central nervous system administration of CNS drugs with a short half-life may require frequent maintenance dosing. The plasma elimination half-life of (1S,3S)-3-amino-4-(difluoromethylidene)cyclopentane-1-carboxylic acid is between about 4 to 6 hours. $C_{max}$ increases in a dose proportional manner over a range of 5 mg-500 mg; whereas there is a greater than proportional increase in AUCs in the dose range. (S)-3-amino-4-(difluoromethylenyl)cyclopent-1-ene-1-carboxylic acid is between 9 and 10 times more potent as an inactivator of GABA-AT than (1S,3S)-3-amino-4-(difluoromethylidene)cyclopentane-1-carboxylic acid and may exhibit similar pharmacokinetics.

In embodiments, (1S,3S)-3-amino-4-(difluoromethylidene)cyclopentane-1-carboxylic acid may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, (S)-3-amino-4-(difluoromethylenyl)cyclopent-1-ene-1-carboxylic acid may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, methods include treating tinnitus, acute sensorineural hearing loss, Meniere's disease, Tourette's syndrome, ADHD or addiction by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating tinnitus, acute sensorineural hearing loss, Meniere's disease, Tourette's syndrome, ADHD or addiction by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of tinnitus, acute sensorineural hearing loss, Meniere's disease, Tourette's syndrome, ADHD or addiction. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of tinnitus, acute sensorineural hearing loss, Meniere's disease, Tourette's syndrome, ADHD or addiction. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating tinnitus, acute sensorineural hearing loss, Meniere's disease, Tourette's syndrome, ADHD or addiction may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating tinnitus, acute sensorineural hearing loss, Meniere's disease, Tourette's syndrome, ADHD or addiction can be about 5 to 80 mg per day and can be increased to 150 mg per day. Dosages can be lower for infants and children than for adults. In embodiments, a pediatric dose for treating tinnitus, acute sensorineural hearing loss, Meniere's disease, Tourette's syndrome, ADHD or addiction can be about 0.1 to 50 mg per day once or in 2, 3 or 4 divided doses. In embodiments, a pediatric dose for treating tinnitus can be 0.75 mg/kg/day to 1.5 mg/kg/day. In embodiments, a pediatric dose for treating acute sensorineural hearing loss can be 0.75 mg/kg/day to 1.5 mg/kg/day. In embodiments, a pediatric dose for treating Meniere's disease can be 0.75 mg/kg/day to 1.5 mg/kg/day. In embodiments, a pediatric dose for treating Tourette's syndrome can be 0.75 mg/kg/day to 1.5 mg/kg/day. In embodiments, a pediatric dose for treating ADHD can be 0.75 mg/kg/day to 1.5 mg/kg/day. In embodiments, a pediatric dose for treating addiction can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition. Pharmaceutical compositions (also referred to simply as compositions) herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating tinnitus, acute sensorineural hearing loss, Meniere's disease, Tourette's syndrome, ADHD or addiction are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 1 hour after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 2 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 3 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 4 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 6 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 8, 10, 12, 14, 16, 18, 20, 22 or 24 hours after administration to the subject. In embodiments, the pharmaceutical compositions provide improvement in one or more symptoms of the tinnitus, acute sensorineural hearing loss, Meniere's disease, Tourette's syndrome, ADHD or addiction the next day after administration to the subject. For example, the pharmaceutical compositions may provide improvement in one or more symptoms of the tinnitus, acute sensorineural hearing loss, Meniere's disease, Tourette's syndrome, ADHD or addiction for more than about, e.g., 2 hours, 4 hours, 6 hours, 8 hours, 10 hours, 12 hours, 14 hours, 16 hours, 18 hours, 20 hours, 22 hours or 24 hours after administration at bedtime or earlier, and waking from a night of sleep.

In embodiments, (1S,3S)-3-amino-4-difluoromethylenyl-1-cyclopentanoic acid or a pharmaceutically acceptable salt thereof is administered to a subject having tinnitus, acute sensorineural hearing loss, Meniere's disease, Tourette's syndrome, ADHD or addiction in combination with (S)-3-amino-4-(difluoromethylenyl)cyclopent-1-ene-1-carboxylic acid or a pharmaceutically acceptable salt thereof. In embodiments, (1S,3S)-3-amino-4-difluoromethylenyl-1-cyclopentanoic acid or a pharmaceutically acceptable salt thereof, or (S)-3-amino-4-(difluoromethylenyl)cyclopent-1-ene-1-carboxylic acid or a pharmaceutically acceptable salt thereof, may be administered to a subject having tinnitus, acute sensorineural hearing loss, Meniere's disease, Tourette's syndrome, ADHD or addiction in separate dosage forms or combined in one dosage form. In embodiments, (1S,3S)-3-amino-4-difluoromethylenyl-1-cyclopentanoic acid or a pharmaceutically acceptable salt thereof, or (S)-3-amino-4-(difluoromethylenyl)cyclopent-1-ene-1-carboxylic acid or a pharmaceutically acceptable salt thereof, may be administered to a subject having tinnitus, acute sensorineural hearing loss, Meniere's disease, Tourette's syndrome, ADHD or addiction simultaneously or at spaced apart intervals.

In embodiments, methods include treating tinnitus, acute sensorineural hearing loss, Meniere's disease, Tourette's syndrome, ADHD or addiction by administering to a subject in need thereof about 0.005 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.005 and 1000 mg/day, or 0.005 mg/kg/day to 14 mg/kg/day, for treatment of tinnitus, acute sensorineural hearing loss, Meniere's disease, Tourette's syndrome, ADHD or addiction. For example, the daily dosage can be, e.g., in the range of about 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 6 mg, 7 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions may include (S)-3-amino-4-(difluoromethylenyl)cyclopent-1-ene-1-carboxylic acid or a pharmaceutically acceptable salt thereof in an amount of, e.g., about 0.001 to 500 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.05 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.01 mg, 0.025 mg, 0.05 mg, 0.075 mg, 0.1 mg, 0.25 mg, 0.5 mg, 0.75 mg, 1 mg, 2 mg, 2.5 mg, 3 mg, 4 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 7.5 mg/per day, 5.5 mg/per day, 5 mg/per day, 4.5 mg/per day, 4 mg/per day, 3.5 mg/per day, 3 mg/per day, 2.5 mg/per day, 2 mg/per day, 1.5 mg/per day, 1 mg/per day, 0.5 mg/per day, 0.25 mg/per day, in one or more doses. In embodiments, an adult dose for treating tinnitus, acute sensorineural hearing loss, Meniere's disease, Tourette's syndrome, ADHD or addiction can be about 0.5 to 50 mg per day and can be increased to 75 mg per day. Dosages can be lower for children than for adults. In embodiments, a pediatric dose for treating tinnitus, acute sensorineural hearing loss, Meniere's disease, Tourette's syndrome, ADHD or addiction can be from about 0.01 to 10 mg per day once or in 2, 3 or 4 divided doses. In embodiments, a pediatric dose for treating tinnitus, acute sensorineural hearing loss, Meniere's disease, Tourette's syndrome, ADHD or addiction can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered via a pharmaceutical composition. In embodiments, as discussed below, various dosage forms including conventional formulations and modified release formulations containing (S)-3-amino-4-(difluoromethylenyl)cyclopent-1-ene-1-carboxylic acid or a pharmaceutically acceptable salt thereof can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating tinnitus, acute sensorineural hearing loss, Meniere's disease, Tourette's syndrome, ADHD or addiction are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 1 hour after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 2 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 3 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 4 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 6 hours after administration to the subject. In embodiments, methods of treating tinnitus, acute sensorineural hearing loss, Meniere's disease, Tourette's syndrome, ADHD or addiction are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the tinnitus, acute sensorineural hearing loss, Meniere's disease, Tourette's syndrome, ADHD or addiction for more than 8, 10, 12, 14, 16, 18, 20, 22 or 24 hours after administration to the subject. In embodiments, the pharmaceutical compositions provide improvement of next day functioning of the subject. For example, the pharmaceutical compositions may provide improvement in one or more symptoms of the tinnitus, acute sensorineural hearing loss, Meniere's disease, Tourette's syndrome, ADHD or addiction for more than about, e.g., 2 hours, 4 hours, 6 hours, 8 hours, 10 hours, 12 hours, 14 hours, 16 hours, 18 hours, 20 hours, 22 hours or 24 hours after administration at bedtime or earlier, and waking from a night of sleep.

In embodiments, (S)-3-amino-4-(difluoromethylenyl)cyclopent-1-ene-1-carboxylic acid or a pharmaceutically acceptable salt thereof or a pharmaceutically acceptable salt thereof is administered to a subject having tinnitus, acute sensorineural hearing loss, Meniere's disease, Tourette's syndrome, ADHD or addiction in combination with (1S,3S)-3-amino-4-difluoromethylenyl-1-cyclopentanoic acid or a pharmaceutically acceptable salt thereof. In embodiments, (S)-3-amino-4-(difluoromethylenyl)cyclopent-1-ene-1-carboxylic acid or a pharmaceutically acceptable salt thereof, or (1S,3S)-3-amino-4-difluoromethylenyl-1-cyclopentanoic acid or a pharmaceutically acceptable salt thereof, may be administered to a subject having tinnitus, acute sensorineural hearing loss, Meniere's disease, Tourette's syndrome, ADHD or addiction in separate dosage forms or combined in one dosage form. In embodiments, (S)-3-amino-4-(difluoromethylenyl)cyclopent-1-ene-1-carboxylic acid or a pharmaceutically acceptable salt thereof, or (1S,3S)-3-amino-4-difluoromethylenyl-1-cyclopentanoic acid or a pharmaceutically acceptable salt thereof, may be administered to a subject having tinnitus, acute sensorineural hearing loss, Meniere's disease, Tourette's syndrome, ADHD or addiction simultaneously or at spaced apart intervals.

In embodiments, provided herein are methods of treating tinnitus, acute sensorineural hearing loss, Meniere's disease, Tourette's syndrome, ADHD or addiction including administering to a subject in need thereof (1 S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, is reduced by more than 50% and the method provides improvement in the subject for more than 10, 12, 14, 16, 18, 20, 22 or 24 hours after administration. In embodiments, provided herein are methods of treating tinnitus, acute sensorineural hearing loss, Meniere's disease, Tourette's syndrome, ADHD or addiction including administering to a subject in need thereof (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, is reduced by more than 50% and the method provides improvement in the subject for more than 10, 12, 14, 16, 18, 20, 22 or 24 hours after administration.

In embodiments, provided herein are methods of treating tinnitus, acute sensorineural hearing loss, Meniere's disease, Tourette's syndrome, ADHD or addiction including administering to a subject in need thereof (1 S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid, or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, is reduced by more than 55% and the method provides improvement in the subject for more than 10, 12, 14, 16, 18, 20, 22 or 24 hours after administration. In embodiments, provided herein are methods of treating tinnitus, acute sensorineural hearing loss, Meniere's disease, Tourette's syndrome, ADHD or addiction including administering to a subject in need thereof (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, is reduced by more than 55% and the method provides improvement in the subject for more than 10, 12, 14, 16, 18, 20, 22 or 24 hours after administration.

In embodiments, provided herein are methods of treating tinnitus, acute sensorineural hearing loss, Meniere's disease, Tourette's syndrome, ADHD or addiction including administering to a subject in need thereof (1 S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, is reduced by more than 60% and the method provides improvement in the subject for more than 10, 12, 14, 16, 18, 20, 22 or 24 hours after administration. In embodiments, provided herein are methods of treating tinnitus, acute sensorineural hearing loss, Meniere's disease, Tourette's syndrome, ADHD or addiction including administering to a subject in need thereof (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, is reduced by more than 60% and the method provides improvement in the subject for more than 10, 12, 14, 16, 18, 20, 22 or 24 hours after administration.

In embodiments, provided herein are methods of treating tinnitus, acute sensorineural hearing loss, Meniere's disease, Tourette's syndrome, ADHD or addiction including administering to a subject in need thereof (1 S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, is reduced by more than 65% and the method provides improvement in the subject for more than 10, 12, 14, 16, 18, 20, 22 or 24 hours after administration. In embodiments, provided herein are methods of treating tinnitus, acute sensorineural hearing loss, Meniere's disease, Tourette's syndrome, ADHD or addiction including administering to a subject in need thereof (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, is reduced by more than 65% and the method provides improvement in the subject for more than 10, 12, 14, 16, 18, 20, 22 or 24 hours after administration.

In embodiments, provided herein are methods of treating tinnitus, acute sensorineural hearing loss, Meniere's disease, Tourette's syndrome, ADHD or addiction wherein the amount of active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about 4 hours after administration of the pharmaceutical composition is less than about 75% of the administered dose. In embodiments, provided herein are methods wherein the amount of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about, e.g., 6 hours, 8 hours, 10 hours, 12 hours, 15 hours, or 20 hours after administration of the pharmaceutical composition is less than about 75%.

In embodiments, provided herein are methods of treating tinnitus, acute sensorineural hearing loss, Meniere's disease, Tourette's syndrome, ADHD or addiction wherein the amount of active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about 4 hours after administration of the pharmaceutical composition is less than about 80% of the administered dose. In embodiments, provided herein are methods wherein the amount of active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about, e.g., 6 hours, 8 hours, 10 hours, 12 hours, 15 hours, or 20 hours after administration of the pharmaceutical composition is less than about 80% of the administered dose.

In embodiments, provided herein are methods of treating tinnitus, acute sensorineural hearing loss, Meniere's disease, Tourette's syndrome, ADHD or addiction wherein the amount of active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about 4 hours after administration of the pharmaceutical composition is between about 65% to about 85% of the administered dose. In embodiments, the amount of active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject after about, e.g., 6 hours, 8 hours, 10 hours, 12 hours, 15 hours, or 20 hours after administration of the pharmaceutical composition is between about 65% to about 85% of the administered dose.

In embodiments, the pharmaceutical compositions described herein may be administered once daily, twice daily, three times daily, four times daily, or every other day. In embodiments, the pharmaceutical compositions described herein may be administered by continuous infusion. In embodiments, a pharmaceutical composition described herein is provided to the subject in the morning. In embodiments, a pharmaceutical composition described herein is provided to the subject in the evening. In embodiments, a pharmaceutical composition described herein is provided to the subject once in the evening and once in the morning. In embodiments, a pharmaceutical composition described herein is provided to the subject once in the morning, once in the afternoon and once in the evening.

In embodiments, as mentioned previously, pharmaceutical compositions herein may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Some subjects with tinnitus, acute sensorineural hearing loss, Meniere's disease, Tourette's syndrome, ADHD or addiction may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which one or both of (1S,3S)-3-amino-4-(difluoromethylidene)cyclopentane-1-carboxylic acid, (S)-3-amino-4-(difluoromethylenyl)cyclopent-1-ene-1-carboxylic acid (KT-II-115), or a pharmaceutically acceptable salt of any of the preceding, is applied to beads, e.g., confectioners nonpareil beads, and then coated with conventional release retarding materials such as waxes, enteric coatings and the like. In embodiments, beads can be formed in which one or both of (1S,3 S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are known to those skilled in the art. For example, coated delayed release beads or granules in which one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, is applied to beads, e.g., confectioners nonpareil beads, and then coated with conventional release delaying materials such as waxes, enteric coatings and the like. In embodiments, beads can be formed in which one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets.

In embodiments, one both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, is incorporated into porous inert carriers that provide delayed release profiles. In embodiments, the porous inert carriers incorporate channels or passages from which the drug diffuses into surrounding fluids. In embodiments, one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, pharmaceutical compositions described herein are suitable for parenteral administration, including, e.g., intramuscular (i.m.), intravenous (i.v.), subcutaneous (s.c.), intraperitoneal (i.p.), or intrathecal (i.t.). Parenteral compositions must be sterile for administration by injection, infusion or implantation into the body and may be packaged in either single-dose or multi-dose containers. In embodiments, liquid pharmaceutical compositions for parenteral administration to a subject include an active substance, e.g., (1S,3S)-3-amino-4-(difluoromethylidene)cyclopentane-1-carboxylic acid, (S)-3-amino-4-(difluoromethylenyl)cyclopent-1-ene-1-carboxylic acid (KT-II-115), or a pharmaceutically acceptable salt of any of the preceding, in any of the respective amounts described above. In embodiments, the pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, pharmaceutical compositions for parenteral administration include respective amounts described above for (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding. In embodiments, pharmaceutical compositions for parenteral administration include about 0.05 mg to about 500 mg active substance, e.g., (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding. In embodiments, pharmaceutical compositions for parenteral administration to a subject include an active substance, e.g., (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, at a respective concentration of about 0.005 mg/ml to about 500 mg/ml. In embodiments, the pharmaceutical composition for parenteral administration includes an active substance, e.g., (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, at a respective concentration of, e.g., about 0.05 mg/ml to about 50 mg/ml, about 0.1 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for parenteral administration includes an active substance, e.g., (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml.

In embodiments, a pharmaceutical composition for parenteral administration is provided wherein the pharmaceutical composition is stable for at least six months. In embodiments, the pharmaceutical compositions for parenteral administration exhibit no more than about 5% decrease in active substance, e.g., (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, e.g., 3 months or 6 months. In embodiments, the amount of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a subject in need thereof.

The pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, used in the composition. Thus, parenteral compositions are provided wherein there is no incompatibility between any of the components of the dosage form.

In embodiments, parenteral compositions including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, include a stabilizing amount of at least one excipient. For example, excipients may be selected from the group consisting of buffering agents, solubilizing agents, tonicity agents, antioxidants, chelating agents, antimicrobial agents, and preservatives. One skilled in the art will appreciate that an excipient may have more than one function and be classified in one or more defined group.

In embodiments, parenteral compositions including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, thrice or four or more times daily, or continuously depending on the subject's needs.

In embodiments, parenteral compositions of an active substance, e.g., (1S,3 S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, provided herein are methods of treating tinnitus, acute sensorineural hearing loss, Meniere's disease, Tourette's syndrome, ADHD or addiction including administering to a subject in need thereof a pharmaceutical composition including an active substance, e.g., one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in a respective amount described herein, wherein the composition provides an in vivo plasma profile having a $C_{max}$, individually or combined, less than about 800 ng/ml. In embodiments, the composition provides improvement for more than 6 hours after administration to the subject.

In embodiments, pharmaceutical compositions including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, provide an in vivo plasma profile having a $C_{max}$, individually or combined, less than about, e.g., 2000 ng/ml, 1000 ng/ml, 850 ng/ml, 800 ng/ml, 750 ng/ml, 700 ng/ml, 650 ng/ml, 600 ng/ml, 550 ng/ml, 450 ng/ml, 400 ng/ml 350 ng/ml, or 300 ng/ml and wherein the composition provides improvement in symptoms of tinnitus, acute sensorineural hearing loss, Meniere's disease, Tourette's syndrome, ADHD or addiction the next day in the subject. In embodiments, the pharmaceutical composition provides an in vivo plasma profile having a $C_{max}$, individually or combined, less than about, e.g., 250 ng/ml, 200 ng/ml 150 ng/ml, or 100 ng/ml and wherein the composition provides improvement of symptoms of tinnitus, acute sensorineural hearing loss, Meniere's disease, Tourette's syndrome, ADHD or addiction in the subject. In embodiments, the pharmaceutical composition provides improvement in one or more symptoms of tinnitus, acute sensorineural hearing loss, Meniere's disease, Tourette's syndrome, ADHD or addiction for more than 6 hours after administration.

In embodiments, provided herein are methods of tinnitus, acute sensorineural hearing loss, Meniere's disease, Tourette's syndrome, ADHD or addiction including administering to a subject in need thereof a pharmaceutical composition containing one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides a consistent in vivo plasma profile having a $AUC_{0-\infty}$, individually or combined, of less than about 900 ng·hr/ml. In embodiments, the pharmaceutical composition provides improvement in symptoms of tinnitus, acute sensorineural hearing loss, Meniere's disease, Tourette's syndrome, ADHD or addiction the next day. In embodiments, the compositions provide an in vivo plasma profile having a $AUC_{0-\infty}$, individually or combined, of less than about, e.g., 850 ng·hr/ml, 800 ng·hr/ml, 750 ng·hr/ml, or 700 ng·hr/ml and wherein the pharmaceutical composition provides improvement in symptoms of tinnitus, acute sensorineural hearing loss, Meniere's disease, Tourette's syndrome, ADHD or addiction the next day in the subject. In embodiments, the composition provides improvement in one or more symptoms of tinnitus, acute sensorineural hearing loss or Meniere's disease for more than 6 hours after administration.

In embodiments, provided herein are methods of treating tinnitus, acute sensorineural hearing loss, Meniere's disease, Tourette's syndrome, ADHD or addiction including administering to a subject in need thereof a pharmaceutical composition comprising an active substance, e.g., one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the pharmaceutical composition provides an in vivo plasma profile having a $AUC_{0-\infty}$, individually or combined, of less than about, e.g., 650 ng·hr/ml, 600 ng·hr/ml, 550 ng·hr/ml, 500 ng·hr/ml, or 450 ng·hr/ml. In embodiments, the composition provides an in vivo plasma profile having a $AUC_{0-\infty}$, individually or combined, of less than about, e.g., 400 ng·hr/ml, 350 ng·hr/ml, 300 ng·hr/ml, 250 ng·hr/ml, or 200 ng·hr/ml. In embodiments, the pharmaceutical composition provides an in vivo plasma profile having a $AUC_{0-\infty}$, individually or combined, of less than about, e.g., 150 ng·hr/ml, 100 ng·hr/ml, 75 ng·hr/ml, or 50 ng·hr/ml. In embodiments, the pharmaceutical composition provides improvement in symptoms of tinnitus, acute sensorineural hearing loss, Meniere's disease, Tourette's syndrome, ADHD or addiction the next day in the subject, after administration for more than, e.g., 4 hours, 6 hours, 8 hours, 10 hours, or 12 hours, after administration of the composition to the subject.

In embodiments, provided herein are methods of treating tinnitus, acute sensorineural hearing loss, Meniere's disease, Tourette's syndrome, ADHD or addiction including administering to a subject in need thereof a first pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding.

In embodiments, the second pharmaceutical composition provides an in vivo plasma profile having a mean $AUC_{0-\infty}$ which is about the same as the mean $AUC_{0-\infty}$ of the first pharmaceutical composition. In embodiments, the second pharmaceutical composition provides an in vivo plasma profile having a mean $AUC_{0-\infty}$ of at least about 20% less than the first pharmaceutical composition. In embodiments, provided herein are methods of treating tinnitus, acute sensorineural hearing loss, Meniere's disease, Tourette's syndrome, ADHD or addiction including administering to a subject in need thereof a first pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the second pharmaceutical composition provides a stable in vivo plasma profile having a mean $AUC_{0-\infty}$ of at least about, e.g., 25%, 30%, 35%, 40%, 45% or 50% less than the first pharmaceutical composition. In embodiments, the compositions provide improvement in symptoms of tinnitus, acute sensorineural hearing loss, Meniere's disease, Tourette's syndrome, ADHD or addiction in the subject the next day after administration. In embodiments, the pharmaceutical compositions may provide improvement in one or more symptoms for more than about, e.g., 6 hours, 8 hours, 10 hours, 12 hours, 14 hours, 16 hours, 18 hours, 20 hours, 22 hours or 24 hours after administration of the first and/or second pharmaceutical composition.

In embodiments, provided herein are methods of treating tinnitus, acute sensorineural hearing loss, Meniere's disease, Tourette's syndrome, ADHD or addiction including administering to a subject in need thereof a first pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement in symptoms of tinnitus, acute sensorineural hearing loss, Meniere's disease, Tourette's syndrome, ADHD or addiction the next day following administration in the subject. In embodiments, the first pharmaceutical composition provides improvement in one or more symptom for more than, e.g., 6 hours, 8 hours, 10 hours, 12 hours, 14 hours, 16 hours, 18 hours, 20 hours, 22 hours or 24 hours after administration of the first pharmaceutical composition.

In embodiments, provided herein are methods of treating tinnitus, acute sensorineural hearing loss, Meniere's disease, Tourette's syndrome, ADHD or addiction including administering to a subject in need thereof a first pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour. In embodiments, the $T_{max}$ of the first pharmaceutical composition is less than 0.5 hour. In embodiments, the $T_{max}$ of the first pharmaceutical composition is less than 0.25 hour. In embodiments, the $T_{max}$ of the second pharmaceutical composition is less than 3 hours. In embodiments, the $T_{max}$ of the second pharmaceutical composition is less than 2.5 hours. In embodiments, the $T_{max}$ of the second pharmaceutical composition is less than 2 hours. In embodiments, the $T_{max}$ of the second pharmaceutical composition is less than 1.5 hours. In embodiments, the $T_{max}$ of the second pharmaceutical composition is less than 1 hour. In embodiments, the $T_{max}$ of the second pharmaceutical composition is less than 0.5 hour. In embodiments, the $T_{max}$ of the second pharmaceutical composition is less than 0.25 hour.

In embodiments, the first pharmaceutical composition provides a dissolution of at least about 80% within the first 20 minutes of administration to a subject in need thereof. In embodiments, the first pharmaceutical composition provides a dissolution of at least about, e.g., 85%, 90% or 95% within the first 20 minutes of administration to a subject in need thereof. In embodiments, the first pharmaceutical composition provides a dissolution of at least 80% within the first 10 minutes of administration to a subject in need thereof.

In embodiments, administration of the first and second pharmaceutical compositions may be simultaneous or separated by an interval of time to achieve long-term improvement in at least one symptom of tinnitus, acute sensorineural hearing loss, Meniere's disease, Tourette's syndrome, ADHD or addiction. In embodiments, the first and second pharmaceutical composition may be administered 1, 2, 3, 4, 5, 6, 7, 8, 9, 10, 11, or 12 hours apart. In embodiments the first and second pharmaceutical composition may be administered 12 hours apart. In embodiments, the first and second pharmaceutical compositions may administered within, e.g., 15 minutes, 30 minutes, 1 hour, 2 hours, 6 hours, 12 hours, 18 hours, 24 hours, etc. In embodiments, the first and second pharmaceutical compositions may administered separated by at least, e.g., 15 minutes, 30 minutes, 1 hour, 2 hours, 12 hours, 18 hours, 24 hours, etc. In embodiments, improvement in at least one symptom of tinnitus, acute sensorineural hearing loss, Meniere's disease, Tourette's syndrome, ADHD or addiction for more than 8 hours after administration to the subject is provided. In embodiments, improvement for more than about, e.g., 10 hours, 12 hours, 15 hours, 18 hours, 20 hours, 24 hours, 30 hours, 36 hours, 42 hours or 48 hours after administration to the subject is provided.

In embodiments, the administration of the first and second pharmaceutical composition may provide a synergistic effect to improve at least one symptom of tinnitus, acute sensorineural hearing loss, Meniere's disease, Tourette's syndrome, ADHD or addiction.

In embodiments, provided herein are methods of treating tinnitus, acute sensorineural hearing loss, Meniere's disease, Tourette's syndrome, ADHD or addiction including administering to a subject in need thereof a first pharmaceutical dosage including a sub-therapeutic amount of one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding. In embodiments, treating tinnitus, acute sensorineural hearing loss, Meniere's disease, Tourette's syndrome, ADHD or addiction includes administering to a subject in need thereof a first pharmaceutical dosage including a sub-therapeutic amount of one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides improvement in one or more symptoms of tinnitus, acute sensorineural hearing loss or Meniere's disease for more than 6 hours after administration.

In embodiments, the first and/or the second pharmaceutical compositions contain sub-therapeutic dosages. A sub-therapeutic dosage is an amount of active substance, e.g., one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, that is less than the amount typically required for a therapeutic effect. In embodiments, a sub-therapeutic dosage is an amount of one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, that alone may not provide tinnitus, acute sensorineural hearing loss, Meniere's disease, Tourette's syndrome, ADHD or addiction, acute sensorineural hearing loss or Meniere's disease but is sufficient to maintain such improvement. In embodiments, the methods provide administering a first pharmaceutical composition that provides improvement in at least one symptom of tinnitus, acute sensorineural hearing loss, Meniere's disease, Tourette's syndrome, ADHD or addiction and a second composition that maintains the improvement. In embodiments, the second composition contains a sub-therapeutic dose of one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding. In embodiments, after administration of the first pharmaceutical composition, the second pharmaceutical composition may provide a synergistic effect to improve at least one symptom of tinnitus, acute sensorineural hearing loss, Meniere's disease, Tourette's syndrome, ADHD or addiction. In embodiments, the second pharmaceutical composition may provide a synergistic effect to improve at least one symptom of tinnitus, acute sensorineural hearing loss, Meniere's disease, Tourette's syndrome, ADHD or addiction.

In embodiments, provided herein are methods of treating tinnitus, acute sensorineural hearing loss, Meniere's disease, Tourette's syndrome, ADHD or addiction including administering to a subject in need thereof a first pharmaceutical composition including a first pharmaceutical dosage of, e.g., one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the first pharmaceutical dosage provides improvement for more than 6 hours after administration, and a second pharmaceutical composition including a sub-therapeutic dosage of one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding.

In embodiments, the first or the second pharmaceutical composition are provided to the subject once in the evening and once in the morning. In embodiments, the total amount of one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, administered to a subject in a 24-hour period is any of the respective amounts described herein.

In embodiments, the first and/or the second pharmaceutical compositions may be provided with conventional release or modified release profiles. The first and second pharmaceutical compositions may be provided at the same time or separated by an interval of time, e.g., 1 hour, 2 hours, 3 hours, 4 hours, 5 hours, 6 hours, 12 hours, etc. In embodiments, the first and the second pharmaceutical compositions may be provided with different drug release profiles to create a two-phase release profile. For example, the first pharmaceutical composition may be provided with an immediate release profile, e.g., ODDF, parenteral, etc., and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In embodiments, the first pharmaceutical composition is an immediate release composition. In embodiments, the second pharmaceutical composition is an immediate release composition. In embodiments, the first and second pharmaceutical compositions are provided as separate immediate release compositions, e.g., film, tablets or capsules. In embodiments the first and second pharmaceutical compositions are provided 12 hours apart.

It should be understood that respective dosage amounts of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, that are provided herein are applicable to all the dosage forms described herein including conventional dosage forms, modified dosage forms, the first and second pharmaceutical compositions, as well as the parenteral formulations described herein. Those skilled in the art will determine appropriate amounts depending on criteria such as dosage form, route of administration, subject tolerance, efficacy, therapeutic goal and therapeutic benefit, among other pharmaceutically acceptable criteria.

Combination therapies utilizing one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, can include administration of the active agents together in the same admixture, or in separate admixtures. In embodiments, the pharmaceutical composition can includes two, three, or more active agents. In embodiments, the combinations result in a more than additive effect on the treatment of the disease or disorder. Thus, treatment is provided for tinnitus, acute sensorineural hearing loss, Meniere's disease, Tourette's syndrome, ADHD or addiction with a combination of agents that combined, may provide a synergistic effect that enhances efficacy.

In embodiments, a co-therapy of (1S,3S)-3-amino-4-(difluoromethylidene)cyclopentane-1-carboxylic acid and (S)-3-amino-4-(difluoromethylenyl)cyclopent-1-ene-1-carboxylic acid (KT-II-115), or a pharmaceutically acceptable salt of any of the preceding, is effective to reduce frequency or severity of symptoms in the subject greater than any of the compounds administered alone. In embodiments, the co-therapy produces a more than additive result compared to compounds administered individually.

In embodiments, the subject may be started at a low dose and the dosage is escalated. In this manner, it can be determined if the drug is well tolerated in the subject. Dosages can be lower for children than for adults.

In embodiments, provided herein are methods of treating tinnitus including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with a second pharmaceutically active agent. In embodiments, provided herein are methods of treating ASNHL including administering to a patient in need thereof a pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with a second pharmaceutically active agent. In embodiments, provided herein are methods of treating Meniere's disease including administering to a patient in need thereof a pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with a second pharmaceutically active agent. In embodiments, provided herein are methods of treating Tourette's syndrome including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with a second pharmaceutically active agent. In embodiments, provided herein are methods of treating ADHD including administering to a patient in need thereof a pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with a second pharmaceutically active agent. In embodiments, provided herein are methods of treating addiction including administering to a patient in need thereof a pharmaceutical composition including one or both of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with a second pharmaceutically active agent.

The second pharmaceutically active agent may include analgesics, anti-inflammatory agents, antidepressants, calcium channel antagonists, glutamate receptor antagonists, CGRP agonists, CGRP antagonists, anticonvulsants (e.g., baclofen type), osmoregulators, sodium channel blockers, anticonvulsants, antiarrhythmics, and neuroprotectives. In embodiments analgesics may include opioids, non-steroidal analgesics, gabapentin, and alpha-adrenergic agonists. In embodiments, the second active agent may include a sulfonamide, for example, acetazolamide, azosemide, bumetanide, chlorthalidone, clopamide, furosemide, hydrochlorothiazide (HCT, HCTZ, HZT), indapamide, mefruside, metolazone, piretanide, tripamide xipamide, dichlorphenamide (DCP), dorzolamide, ethoxzolamide, sultiame, or zonisamide. In embodiments, the second active agent may include a thiazide, for example, bendroflumethiazide, benzthiazide, chlorothiazide, hydrochlorothiazide, hydroflumethiazide, methylclothiazide, polythiazide, trichlor-methiazide, chlorthalidone, indapamide, metolazone or quinethazone.

In embodiments, the second active agent may include a NK1 receptor antagonist, for example, 2-(S)-(4-fluoro-2-methyl-phenyl)-piperazine-1-carboxylic acid [1-(R)-(3,5-bis-trifluoromethyl-phenyl)-ethyl]-methyl-amide or pharmaceutically acceptable salts or solvates thereof, 4-(S)-(4-acetyl-piperazin-1-yl)-2-(R)-(4-fluoro-2-methyl-phenyl)-piperidine-1-carboxylic acid [1-(R)-(3,5-bis-trifluoromethyl-phenyl)-ethyl]-methylamide or pharmaceutically acceptable salts or solvates thereof, and 2-(R)-(4-fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methyl-amide or pharmaceutically acceptable salts or solvates thereof.

In embodiments, the second active agent may include risperidone, ziprasidone, haloperidol, pimozide, fluphenazine, clonidine or guanfacine. In embodiments, the second active agent may include methylphenidate, methamphetamine, dextroamphetamine, atomoxetine, bupropion, guanfacine, or clonidine. In embodiments, the second active agent may include naltrexone, disulfiram, acamprosate, topiramate, buprenorphine, methadone, gabapentin or pregabalin.

In embodiments, the second active agent may include a benzodiazepine. The benzodiazepine may include diazepam, alprazolam, estazolam, clobazam, clonazepam, clorazepate, chlordiazepoxide, flurazepam, triazolam, temazepam, midazolam, halazepam, quazepam, lorazepam, oxazepam, derivatives thereof, or pharmaceutically acceptable salts thereof.

In embodiments, the second active agent may include clonazepam and/or clobazam. In embodiments, provided herein are methods of treating tinnitus including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in any of the amounts described above and clonazepam. In embodiments, provided herein are methods of treating tinnitus including administering to a patient in need thereof a pharmaceutical composition including ((1 S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding in any of the amounts described above and clobazam. In embodiments, provided herein are methods of treating ASNHL including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in any of the amounts described above and clonazepam. In embodiments, provided herein are methods of treating ASNHL including administering to a patient in need thereof a pharmaceutical composition including (1S, 3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in any of the amounts described above and clobazam. In embodiments, provided herein are methods of treating Meniere's disease including administering to a patient in need thereof a pharmaceutical composition (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in any of the amounts described above and clonazepam. In embodiments, provided herein are methods of treating Meniere's disease including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in any of the amounts described above and clobazam.

The disclosed combinations may provide improved treatment compared to either active agent alone. For example, the combinations may provide synergy, e.g., low dose treatments may be particularly effective in reducing or eliminating symptoms of subjective tinnitus. Likewise, the combinations may provide synergy, e.g., low dose treatments may be particularly effective in reducing or eliminating symptoms of ASNHL. Likewise, the combinations may provide synergy, e.g., low dose treatments may be particularly effective in reducing or eliminating symptoms of Meniere's disease. Likewise, the combinations may provide synergy, e.g., low dose treatments may be particularly effective in reducing or eliminating symptoms of Tourette's syndrome. Likewise, the combinations may provide synergy, e.g., low dose treatments may be particularly effective in reducing or eliminating symptoms of ADHD. Likewise, the combinations may provide synergy, e.g., low dose treatments may be particularly effective in reducing or eliminating symptoms of addiction.

In embodiments, the pharmaceutical compositions include 0.1 mg to 30 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg clobazam or a pharmaceutically acceptable salt thereof In embodiments, the pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg clobazam or a pharmaceutically acceptable salt thereof. In embodiments, the pharmaceutical compositions include 0.1 mg, 0.25 mg, 0.5 mg, 1 mg, 1.5 mg, 2.0 mg, 2.5 mg, 3 mg, 4 mg, 5 mg, 7 mg, 7.5 mg, 8 mg, 8.5 mg, 9 mg, 9.5 mg, 10 mg, 10.5 mg, 11 mg, 12 mg, 12.5 mg, 13 mg, 14 mg, 15 mg, 16 mg, 17 mg, 17.5 mg, 18 mg, 19 mg, 20 mg, 21 mg, 22 mg, 23 mg, 24 mg, 25 mg, 26 mg, 27 mg, 28 mg, 29 mg, or 30 mg clobazam or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg clobazam or a pharmaceutically acceptable salt thereof.

In embodiments, the adult dose of clobazam may be 5-60 mg daily in divided doses or as a single dose given at night. For example, the adult dose of clobazam may be 5-10 mg, 5-20 mg, 5-25 mg, 5-30 mg, 5-35 mg, 5-40 mg, 5-50 mg, 5-55 mg, 10-15 mg, 10-20 mg, 10-25 mg, 10-30 mg, 10-35 mg, 10-40 mg, 10-45 mg, 10-50 mg, 10-55 mg, 10-60 mg, 15-20 mg, 15-25 mg, 15-30 mg, 15-35 mg, 15-40 mg, 15-50 mg, 15-55 mg, 15-60 mg, 20-25 mg, 20-30 mg, 20-35 mg, 20-40 mg, 20-45 mg, 20-50 mg, 20-55 mg, 20-60 mg, 25-30 mg, 25-35 mg, 25-40 mg, 25-50 mg, 25-55 mg, 25-60 mg, 30-35 mg, 30-40 mg, 30-45 mg, 30-50 mg, 30-55 mg, 30-60 mg, 35-40 mg, 35-50 mg, 35-55 mg, 35-60 mg, 40-45 mg, 40-50 mg, 40-55 mg, 40-60 mg, 45-50 mg, 45-55 mg, 45-60 mg, 50-55 mg, or 55-60 mg, daily in divided doses such as twice a day, three times a day, or as a single dose given at night.

In embodiments, provided herein are methods of treating tinnitus including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and clobazam or a pharmaceutically acceptable salt thereof, together or separately, wherein the patient experiences improvement of at least one tinnitus symptom for more than 4 hours after administration of the pharmaceutical composition to the patient. In embodiments, the improvement of at least one tinnitus symptom for more than 6 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement of at least one tinnitus symptom for more than, e.g., 8 hours, 10 hours, 12 hours, 15 hours, 18 hours, 20 hours, or 24 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement in at least one tinnitus symptom for at least e.g., 8 hours, 10 hours, 12 hours, 15 hours, 18 hours, 20 hours, or 24 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement in at least one tinnitus symptom for 12 hours after administration of (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure.

In embodiments, provided herein are methods of treating ASNHL including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and clobazam or a pharmaceutically acceptable salt thereof, together or separately, wherein the patient experiences improvement of at least one ASNHL symptom for more than 4 hours after administration of the pharmaceutical composition to the patient. In embodiments, the improvement of at least one ASNHL symptom for more than 6 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement of at least one ASNHL symptom for more than, e.g., 8 hours, 10 hours, 12 hours, 15 hours, 18 hours, 20 hours, or 24 hours after administration of the ((1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement in at least one ASNHL symptom for at least e.g., 8 hours, 10 hours, 12 hours, 15 hours, 18 hours, 20 hours, or 24 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement in at least one ASNHL symptom for 12 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure.

In embodiments, provided herein are methods of treating Meniere's disease including administering to a patient in need (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and clobazam or a pharmaceutically acceptable salt thereof, together or separately, wherein the patient experiences improvement of at least one Meniere's disease symptom for more than 4 hours after administration of the pharmaceutical composition to the patient. In embodiments, the improvement of at least one Meniere's disease symptom for more than 6 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement of at least one Meniere's disease symptom for more than, e.g., 8 hours, 10 hours, 12 hours, 15 hours, 18 hours, 20 hours, or 24 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement in at least one Meniere's disease symptom for at least e.g., 8 hours, 10 hours, 12 hours, 15 hours, 18 hours, 20 hours, or 24 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure. In embodiments, improvement in at least one Meniere's disease symptom for 12 hours after administration of the (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and the clobazam or a pharmaceutically acceptable salt thereof to the patient is provided in accordance with the present disclosure.

In embodiments, provided herein are methods of treating tinnitus including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof wherein the composition provides improvement of at least one tinnitus symptom for more than 4 hours after administration of the pharmaceutical composition to the patient. In embodiments, the improvement of at least one tinnitus symptom for more than 6 hours after administration of the pharmaceutical composition to the patient is provided in accordance with the present disclosure. In embodiments, improvement of at least one tinnitus symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one tinnitus symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one tinnitus symptom for 12 hours after administration of the pharmaceutical composition to the patient is provided in accordance with the present disclosure.

In embodiments, provided herein are methods of treating ASNHL including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof wherein the composition provides improvement of at least one ASNHL symptom for more than 4 hours after administration of the pharmaceutical composition to the patient. In embodiments, the improvement of at least one ASNHL symptom for more than 6 hours after administration of the pharmaceutical composition to the patient is provided in accordance with the present disclosure. In embodiments, improvement of at least one ASNHL symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one ASNHL symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one ASNHL symptom for 12 hours after administration of the pharmaceutical composition to the patient is provided in accordance with the present disclosure.

In embodiments, provided herein are methods of treating Meniere's disease including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof wherein the composition provides improvement of at least one Meniere's disease symptom for more than 4 hours after administration of the pharmaceutical composition to the patient. In embodiments, the improvement of at least one Meniere's disease symptom for more than 6 hours after administration of the pharmaceutical composition to the patient is provided in accordance with the present disclosure. In embodiments, improvement of at least one Meniere's disease symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one Meniere's disease symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one Meniere's disease symptom for 12 hours after administration of the pharmaceutical composition to the patient is provided in accordance with the present disclosure.

In embodiments, provided herein methods of treating tinnitus including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides improvement in tinnitus the next day. In embodiments, provided herein methods of treating ASNHL including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides improvement in ASNHL the next day. In embodiments, provided herein methods of treating Meniere's disease including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides improvement in Meniere's disease the next day. In embodiments, provided herein methods of treating Tourette's syndrome including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides improvement in Tourette's syndrome the next day. In embodiments, provided herein methods of treating ADHD including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides improvement in ADHD the next day. In embodiments, provided herein methods of treating addiction including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, wherein the composition provides improvement in addiction the next day.

In embodiments, provided herein methods of treating tinnitus including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof, wherein the composition provides improvement in tinnitus the next day. In embodiments, provided herein methods of treating ASNHL including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof, wherein the composition provides improvement in ASNHL the next day. In embodiments, provided herein methods of treating Meniere's disease including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof, wherein the composition provides improvement in Meniere's disease the next day. In embodiments, provided herein methods of treating Tourette's syndrome including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof, wherein the composition provides improvement in Tourette's syndrome the next day. In embodiments, provided herein methods of treating ADHD including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof, wherein the composition provides improvement in ADHD the next day. In embodiments, provided herein methods of treating addiction including administering to a patient in need thereof (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, in combination with clobazam or a pharmaceutically acceptable salt thereof, wherein the composition provides improvement in addiction the next day.

In embodiments, provided herein methods of treating tinnitus including administering to a patient in need thereof a pharmaceutical composition including (1S,3S)-3-amino-4-(difluoromethylidene)cyclopentane-1-carboxylic acid or (S)-3-amino-4-(difluoromethylenyl)cyclopent-1-ene-1-carboxylic acid (KT-II-115), or a pharmaceutically acceptable salt of any of the preceding, and clobazam or a pharmaceutically acceptable salt thereof, wherein the composition provides improvement in tinnitus the next day.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of tinnitus, ASNHL, Meniere's disease, Tourette's syndrome, ADHD or addiction measured relative to at least one symptom.

"Improvement in one or more symptoms of tinnitus, ASNHL, Meniere's disease, Tourette's syndrome, ADHD or addiction a day after administration" refers to improvement wherein the beneficial effect of at least one symptom lasts over a period of time, e.g., 6 hours, 12 hours, 24 hours etc.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml). The area under the curve is governed by clearance. Clearance is defined as the volume of blood or plasma that is totally cleared of its content of drug per unit time (ml/min).

"Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate aspects of the disclosure herein.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" means a dosage sufficient to alleviate one or more symptoms of a disorder, disease, or condition being treated e.g., tinnitus, ASNHL, Meniere's disease, Tourette's syndrome, ADHD or addiction, or to otherwise provide a desired pharmacological and/or physiologic effect.

"Co-administered with", "co-therapy", "in combination with", "a combination of", "combined with" or "administered along with" may be used interchangeably and mean that two or more agents are administered in the course of therapy. The agents may be administered together at the same time or separately in spaced apart intervals. The agents may be administered in a single dosage form or in separate dosage forms.

"Patient in need thereof" includes individuals that have been diagnosed tinnitus, ASNHL, Meniere's disease, Tourette's syndrome, ADHD or addiction. The methods may be provided to any individual including, e.g., wherein the patient is a neonate, infant, a pediatric patient (6 months to 12 years), an adolescent patient (age 12-18 years) or an adult (over 18 years). "Patient" and "subject" are used interchangeably herein. It should be understood that infants can receive a pediatric dose.

EXAMPLES

The Examples provided herein are included solely for augmenting the disclosure herein and should not be considered to be limiting in any respect.

Example 1

Prospective Assessment of the Efficacy of (S)-3-amino-4-(difluoromethylenyl)cyclopent-1-ene-1-carboxylic acid in Patients with Tinnitus This study is designed to determine whether (S)-3-amino-4-(difluoromethylenyl)cyclopent-1-ene-1-carboxylic acid leads to an improvement in tinnitus. The primary objective of this study may be to evaluate the safety and tolerability from Baseline to Week 6 and Week 12 of (S)-3-amino-4-(difluoromethylenyl)cyclopent-1-ene-1-carboxylic acid in adult subjects with tinnitus across different dose levels and in two dosing schedules. The following dosing schedules may be tested against placebo: (1) Once daily (o.d.): An evening dose; and (2) Twice daily (b.i.d.): Evening and morning doses titrated to target doses. The safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine); (4) Suicidality assessed by ABC-Irritability Subscale; (5) EEG (change in background frequency, intensity of epileptiform discharges); and/or (6) Caregivers may maintain an electronic seizure diary (on same device as sleep log).

The secondary objective of this study may include the identification of a set of parameters that may best characterize the efficacy of (S)-3-amino-4-(difluoromethylenyl)cyclopent-1-ene-1-carboxylic acid in adult tinnitus subjects for subsequent efficacy trials. These tests may be administered at four full day site visits (Screening, Baseline, Interim and End of Treatment) by an appropriately trained professional to provide the test to an adult tinnitus patient. Assessments may be based on patient's perception of symptoms. Tinnitus loudness—visual analogue scale (VAS) [Time Frame: each week: the time between the questionnaire results at the beginning and compared to the results after each week following initial administration. Tinnitus loudness scale: A range of 1-10 scale. the patients choose which number reflects the loudness of the subjective tinnitus which the patients suffer from. the higher the number—the louder the tinnitus. Tinnitus suffer scale: A range of 1-10 scale. the patient choose which number reflects the best the degree in which the tinnitus causes the patient to suffer. the higher the score—the worse is the tinnitus.

Evaluation of sleep may include analysis by actigraphy to measure: (1) Sleep Onset Latency (SOL); (2) Total Sleep Time (TST); (3) Wake After Sleep Onset (WASO)=total # of wake epochs after sleep onset; (4) Nocturnal Awakenings (NA); and/or (5) Sleep Efficiency=total sleep time (TST) of time in bed (TIB). Additional evaluation of sleep may include analysis of parent/caregiver logs of sleep patterns that may include: (1) bed time; (2) time of sleep onset; (3) number and duration of awakenings; (4) number of disruptive behavior; (5) time of last awakening; and (6) daytime sleepiness.

This study may include three treatment groups. For example, a total of approximately 75 subjects may be enrolled and at the completion of the study, there may be approximately 25 subjects in each of the three treatment groups: 1) single evening dose 2) morning and evening dose and 3) placebo.

All subjects may receive a morning dose (either active or placebo) and an evening dose (either active or placebo) during the entire duration of treatment. For example, two dosing schedules of (S)-3-amino-4-(difluoromethylenyl)cyclopent-1-ene-1-carboxylic acid may be tested: a single evening dose (o.d.) and a morning plus evening dose (b.i.d) designed to provide a more sustained exposure. Schedule C is morning and evening placebo. All subjects may be up-titrated to the target dose unless this target dose is not tolerated (titration conventions described below). All subjects may receive treatment for a maximum of 12 weeks at their optimal tolerated dose.

Doses may be progressively increased in increments (active or placebo) to a target dose (in the evening), and morning dose. Each dose escalation may be performed after adequate tolerability has been assessed by caregiver and investigator. For example, treatment initiation at Day 1 with 1 dose (active (Act) or placebo (Plc)) in the evening. Then target up-titration may begin at Day 3 (window+2 days): If no adverse event (AE) related to the study drug is observed by caregiver and/or the investigator, another dose (active or placebo) is added in the evening. Again at Day 7 (window+2 days), Day 10 (window+2 days and Day 14 (window+2 days) if no AE related to the study drug is observed by caregiver and/or the investigator, another dose (active or placebo) may be added in the morning.

Slowed up-titration or delayed up titration will be acceptable if tolerability does not allow immediate further dose-escalation at any of the above detailed days (3, 7, 10, 14). Down-titration in the case tolerability is not acceptable after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached the subject may be kept stable until End of Treatment visit (week 12) unless intolerability requires down-titration.

All subjects will be screened for participation in the study up to 28 days prior to the first dose administration. Inclusion criteria may include one or more of the following: (1) Age ≥18 years, ≤40 years; (2) Must possess a clinical diagnosis of tinnitus. Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

Example 2

Prospective Assessment of the Efficacy of (S)-3-amino-4-(difluoromethylenyl)cyclopent-1-ene-1-carboxylic acid and Clobazam in Patients with Tinnitus This study is designed to determine whether (S)-3-amino-4-(difluoromethylenyl)cyclopent-1-ene-1-carboxylic acid in combination with clobazam leads to an improvement in tinnitus. The primary objective of this study may be to evaluate the safety and tolerability from Baseline to Week 6 and Week 12 of (S)-3-amino-4-(difluoromethylenyl)cyclopent-1-ene-1-carboxylic acid and clobazam in adult subjects with tinnitus across different dose levels and in two dosing schedules. The following dosing schedules may be tested against placebo: (1) Once daily (o.d.): A dose of (S)-3-amino-4-(difluoromethylenyl)cyclopent-1-ene-1-carboxylic acid at night and clobazam 10 mg unless not tolerated; and (2) Twice daily (b.i.d.): Night and morning doses of (S)-3-amino-4-(difluoromethylenyl)cyclopent-1-ene-1-carboxylic acid and a clobazam 10 mg nighttime dose and (S)-3-amino-4-(difluoromethylenyl)cyclopent-1-ene-1-carboxylic acid and a clobazam 10 mg morning dose unless not tolerated.

The Safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine); (4) Suicidality assessed by ABC-Irritability Subscale; (5) EEG (change in background frequency, intensity of epileptiform discharges); and/or (6) Caregivers may maintain an electronic seizure diary (on same device as sleep log).

The secondary objective of this study may include the identification of a set of parameters that may best characterize the efficacy of (S)-3-amino-4-(difluoromethylenyl)cyclopent-1-ene-1-carboxylic acid in combination with clobazam in adult tinnitus subjects for subsequent efficacy trials. These tests may be administered at four full day site visits (Screening, Baseline, Interim and End of Treatment) by an appropriately trained professional to provide the test to an adult tinnitus patient. Assessments may be based on patient's perception of symptoms.

Tinnitus loudness—visual analogue scale (VAS) [Time Frame: each week: the time between the questionnaire results at the beginning and compared to the results after each week following initial administration. Tinnitus loudness scale: A range of 1-10 scale. the patients choose which number reflects the loudness of the subjective tinnitus which the patients suffer from. the higher the number—the louder the tinnitus. Tinnitus suffer scale: A range of 1-10 scale. the patient choose which number reflects the best the degree in which the tinnitus causes the patient to suffer. the higher the score—the worse is the tinnitus.

Evaluation of sleep may include analysis by actigraphy to measure: (1) Sleep Onset Latency (SOL); (2) Total Sleep Time (TST); (3) Wake After Sleep Onset (WASO)=total # of wake epochs after sleep onset; (4) Nocturnal Awakenings (NA); and/or (5) Sleep Efficiency=total sleep time (TST) of time in bed (TM). Additional evaluation of sleep may include analysis of parent/caregiver logs of sleep patterns that may include: (1) bed time; (2) time of sleep onset; (3) number and duration of awakenings; (4) number of disruptive behavior; (5) time of last awakening; and (6) daytime sleepiness.

This study may include three treatment groups. For example, a total of approximately 75 subjects may be enrolled and at the completion of the study, there may be approximately 25 subjects in each of the three treatment groups: 1) single nighttime dose 2) morning and nighttime dose and 3) placebo.

All subjects may receive a morning dose (either active or placebo) and an evening dose (either active or placebo) during the entire duration of treatment. For example, two dosing schedules of (S)-3-amino-4-(difluoromethylenyl)cyclopent-1-ene-1-carboxylic acid and clobazam may be tested: a single evening dose (o.d.) and a morning plus evening dose (b.i.d.) designed to provide a more sustained exposure. Schedule C is morning and evening placebo. All subjects may be up-titrated to the target dose unless this target dose is not tolerated (titration conventions described below). All subjects may receive treatment for a maximum of 12 weeks at their optimal tolerated dose.

Doses may be progressively increased in increments (active or placebo) to a target dose of 1 nighttime dose, and 1 morning dose in schedule B. Each dose escalation may be performed after adequate tolerability has been assessed by caregiver and investigator. For example, treatment initiation at Day 1 with 1 dose (active (Act) or placebo (Plc)) in the evening. Then target up-titration may begin at Day 3 (window+2 days): If no adverse event (AE) related to the study drugs are observed by caregiver and/or the investigator, another dose (active or placebo) is added in the evening. Again at Day 7 (window+2 days), Day 10 (window+2 days and Day 14 (window+2 days) if no AE related to the study drugs are observed by caregiver and/or the investigator, another dose (active or placebo) may be added in the morning.

Slowed up-titration or delayed up titration will be acceptable if tolerability does not allow immediate further dose-escalation at any of the above detailed days (3, 7, 10, 14). Down-titration in the case tolerability is not acceptable after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached (1 dose in the morning and 1 in the evening) the subject may be kept stable until End of Treatment visit (week 12) unless intolerability requires down-titration.

All subjects will be screened for participation in the study up to 28 days prior to the first dose administration. Inclusion criteria may include one or more of the following: (1) Age ≥18 years, ≤40 years; (2) Must possess a clinical diagnosis of tinnitus. Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

It should be understood that the examples and embodiments provided herein are exemplary examples and embodiments. Those skilled in the art will envision various modifications of the examples and embodiments that are consistent with the scope of the disclosure herein. Such modifications are intended to be encompassed by the claims.

What is claimed is:

1. A method of treating tinnitus which is not secondary to Tourette syndrome, epilepsy and addiction comprising administering to a subject with tinnitus (S)-3-amino-4-(difluoromethylenyl)cyclopent-1-ene-1-carboxylic acid or a pharmaceutically acceptable salt thereof in an amount of from 0.01 mg to 75 mg.

2. The method of treating tinnitus which is not secondary to Tourette syndrome, epilepsy and addiction according to claim 1, wherein the subject is administered from 0.1 mg to 50 mg of (S)-3-amino-4-(difluoromethylenyl)cyclopent-1-ene-1-carboxylic acid or a pharmaceutically acceptable salt thereof.

3. The method of treating tinnitus which is not secondary to Tourette syndrome, epilepsy and addiction according to claim 1, wherein the subject is administered from 0.1 mg to 10 mg of (S)-3-amino-4-(difluoromethylenyl)cyclopent-1-ene-1-carboxylic acid or a pharmaceutically acceptable salt thereof.

4. The method of treating tinnitus which is not secondary to Tourette syndrome, epilepsy and addiction according to claim 1, wherein the total amount of (S)-3-amino-4-(difluoromethylenyl)cyclopent-1-ene-1-carboxylic acid or a pharmaceutically acceptable salt thereof administered to the subject in a twenty-four hour period is between 1 mg and 10 mg.

5. The method of treating tinnitus which is not secondary to Tourette syndrome, epilepsy and addiction according to claim 1, wherein (S)-3-amino-4-(difluoromethylenyl)cyclopent-1-ene-1-carboxylic acid or a pharmaceutically acceptable salt thereof is administered from one to four times a day.

6. The method of treating tinnitus which is not secondary to Tourette syndrome, epilepsy and addiction according to claim 1, wherein administering is accomplished via a route selected from the group consisting of oral, buccal, sublingual, rectal, topical, intranasal, vaginal and parenteral.

7. The method of treating tinnitus which is not secondary to Tourette syndrome, epilepsy and addiction according to claim 1, wherein the method provides improvement in at least one symptom selected from the group consisting of ringing, roaring, static, buzzing, hissing, whooshing, cricket noises, jackhammer noises and/or whistling in one or both ears.

* * * * *